United States Patent [19]
Dobelmann

[11] Patent Number: 6,129,844
[45] Date of Patent: Oct. 10, 2000

[54] WASTE WATER PURIFICATION PROCESS

[76] Inventor: Jan Kai Dobelmann, Waldhornstrasse 30, 76131 Karlsruhe, Germany

[21] Appl. No.: 09/308,847

[22] PCT Filed: Nov. 14, 1997

[86] PCT No.: PCT/DE97/02716

§ 371 Date: May 24, 1999

§ 102(e) Date: May 24, 1999

[87] PCT Pub. No.: WO98/23541

PCT Pub. Date: Jun. 4, 1998

[30] Foreign Application Priority Data

Nov. 26, 1996 [DE] Germany .......................... 196 48 860

[51] Int. Cl.[7] .................................. C02F 3/28; C02F 3/32
[52] U.S. Cl. ........................ 210/602; 210/603; 210/610; 210/614
[58] Field of Search ..................... 210/602, 603, 210/610, 611, 614, 623, 626, 631

[56] References Cited

U.S. PATENT DOCUMENTS

| | | | |
|---|---|---|---|
| 3,986,932 | 10/1976 | Brushwyler et al. | 210/614 |
| 4,134,830 | 1/1979 | Skogman et al. | 210/603 |
| 4,349,435 | 9/1982 | Ochini | 210/614 |
| 4,415,450 | 11/1983 | Wolverton | 210/602 |
| 4,439,315 | 3/1984 | Whiteside | 210/90 |
| 4,626,354 | 12/1986 | Hollman et al. | 210/603 |
| 4,692,249 | 9/1987 | Hammel | 210/603 |
| 4,885,094 | 12/1989 | Srinivasan et al. | 210/610 |
| 5,015,384 | 5/1991 | Burke | 210/603 |
| 5,078,882 | 1/1992 | Northrop | 210/602 |
| 5,137,625 | 8/1992 | Wolverton | 210/195.1 |
| 5,637,218 | 6/1997 | Kick stoh | 210/602 |
| 5,736,047 | 4/1998 | Ngo | 210/602 |
| 5,811,008 | 9/1998 | Von Nordenskjold | 210/614 |

FOREIGN PATENT DOCUMENTS

WO 93/06050 4/1993 WIPO.

OTHER PUBLICATIONS

Teubner, "Abwassertechnik", (ISBN 3–519–45216–2, 9. Auflage) pp. 54–58, Stuttgart (1989) Germany.

*Primary Examiner*—Christopher Upton
*Attorney, Agent, or Firm*—Christie, Parker & Hale, LLP

[57] ABSTRACT

The invention relates to a process for cleaning waste water in which, before the anaerobic treatment as a first stage, biomass produced in the second stage, a plant clarifying unit, is added. Thus, an increase in the organic load in the arriving waste water is achieved and thus loading sufficient for the anaerobic methane digestion is achieved. The lightly loaded waste water exiting from the first stage is used in the plant clarifying part (second stage) for irrigation and fertilization. Under the influence of solar energy, this forms plant biomass which is metered in before the first stage.

Through the process according to the invention it is possible to use lightly loaded organic waste water for an anaerobic methane digestion for cleaning and simultaneous production of biogas.

16 Claims, 1 Drawing Sheet

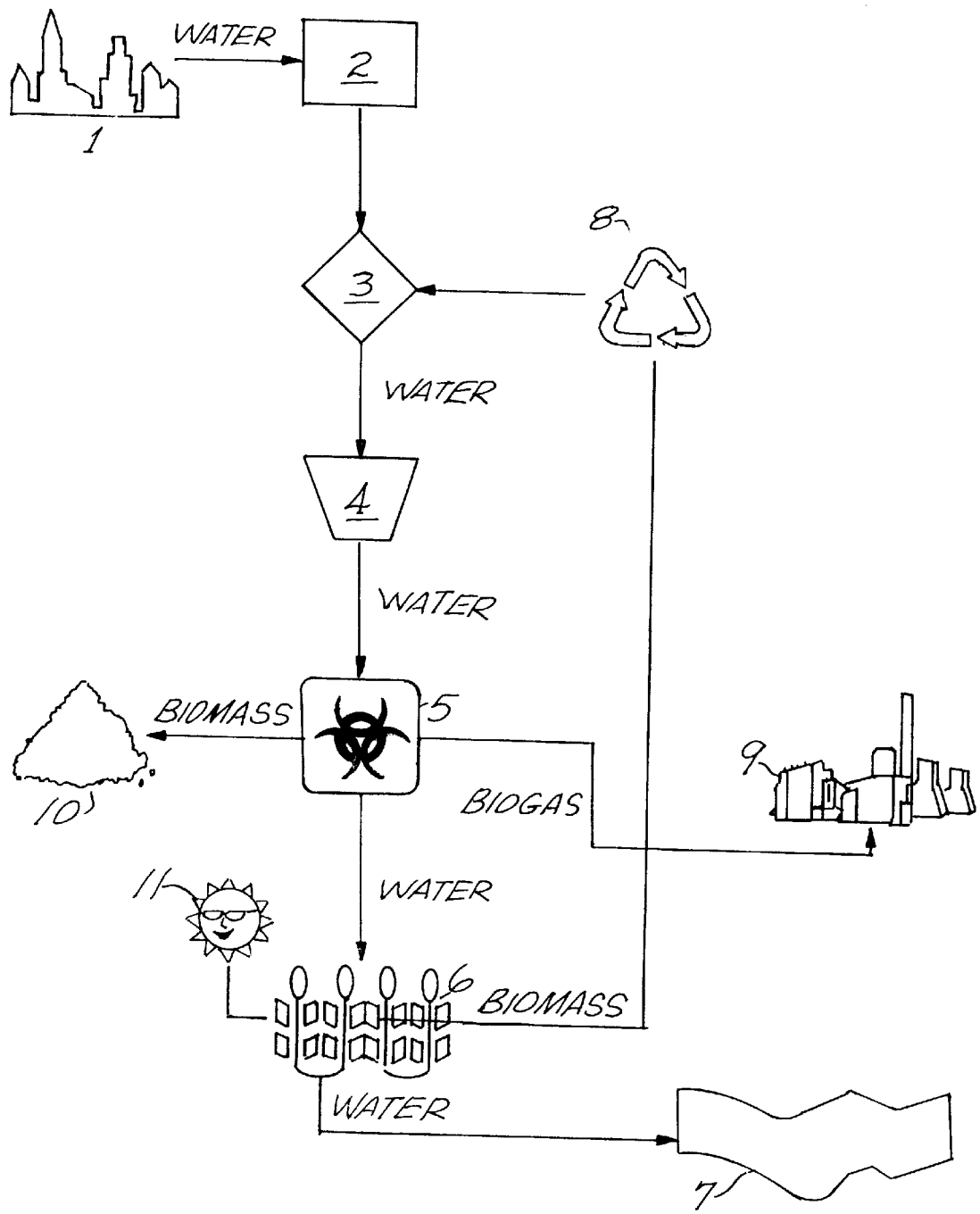

WASTE WATER PURIFICATION PROCESS

FIELD OF THE INVENTION

The invention relates to a method for the treatment of waste water in a two-stage process with simultaneous recovery of energy in the form of biogas.

BACKGROUND OF THE INVENTION

For anaerobic waste water cleaning, different methods and reactors of diverse construction such as UASB, fixed bed reactors, and anaerobic activation chambers, among others, are known.

These reactors are particularly used for industrial waste waters highly loaded with organic material.

SUMMARY OF THE INVENTION

The invention is based on the objective of developing an energy-producing treatment method using anaerobic fermentation for waste water with a low load of organic materials (CSB<500 mg/l).

According to the invention, the objective is solved with a two-stage process method that consists of anaerobic treatment with the production of methane containing biogas as a first cleaning stage, and a plant clarifying unit as a second cleaning stage, where the biomass gathered in the plant clarifying unit is introduced, before the first cleaning stage, into the waste water to be treated. Beside the biomass gathered from the second cleaning stage, additional other organic or inorganic materials and wastes can be introduced into the waste water before the first cleaning step.

Through the method according to the invention, it is possible to make waste water with a low content of organic materials accessible through anaerobic methane digestion.

Before the biomass resulting from the second stage and any additional other organic or inorganic materials and waste are introduced before the first stage into the waste water, they are prepared by being crushed or pulped in a form necessary for the digestion. For the crushing and pulping of the biomass and the other wastes, methods known per se are used such as the FIMA system, ULTRA TURAX amongst others. After the intentional introduction of the biomass resulting from the second stage into the waste water before the first stage, the organic load in the waste water becomes so high that an anaerobic methane digestion is possible. Thus an energy-producing cleaning of waste water that is lightly loaded with organic materials is achieved in which an energy containing gas (combustion value 20–25 MJ/m$^3$), which can be energetically used in numerous ways, is produced. The usual supply of oxygen, associated with energy, which is necessary for aerobic processes, can be omitted.

The quantity, to be added, of the biomass resulting from the second cleaning stage and possibly other biomasses, depends on the loading of the incoming waste water. Thus, it is possible to keep the loading of the waste water admitted to the first cleaning stage constant. The second cleaning stage is protected against overloading and there will thus be no unclarified through-flow of waste water through the second cleaning stage.

If the load in the incoming waste water is high, then the introduction of biomass from both the biomass gathered from the plant biomass in the second cleaning stage and further additional biomasses, can be completely or partially omitted. In these variants there will be a constant throughflow rate in the first cleaning stage.

Preferably, the process according to the invention will be operated so that the waste water admitted to the first cleaning stage has a load with a CSB-value of about 300 mg/l.

Likewise, it is possible to deal with a larger load in the waste water by an extended residence time in the first cleaning stage in order to reach the desired loading value of the waste water leaving the first cleaning stage.

With the process according to the invention it is possible to make use of unused plant biomass from prior art plant clarification systems in the cleaning process.

BRIEF DESCRIPTION OF THE DRAWING

The features and advantages of the invention can be better understood by reference to the following detailed description in conjunction with the accompanying drawing which is a schematic representation of the invention.

DETAILED DESCRIPTION OF THE INVENTION

The invention will be explained with the aid of two process variants. Clearly other embodiments of the invention can exist.

Process variant A relates to an embodiment in which the second cleaning stage is an aquatic plant clarifying unit.

Process variant B relates to an embodiment in which the second cleaning stage is a land treatment unit.

Generally the waste water is transported from the waste water source 1 to the waste water cleaning plant. There, in a first cleaning step, the coarser and finer materials are mechanically separated, for example by settling 2. After this treatment, the crushed biomass is added to the metering position 3 from the storage and granulating container 8, and so the load is raised to an optimal value for the first cleaning step. Material which sinks is removed in a debris chamber 4.

The storage and crushing chamber 8 stores the plant biomass recovered from the second cleaning stage and also the additional organic material and waste. The load-optimized and mechanically cleaned waste water then enters the first cleaning stage, the anaerobic reactor 5. There the decomposable biomass is separated and accumulated in the reactor 5. From the reactor 5, the decomposable biomass is continuously or periodically withdrawn in accordance with the processing method of the reactor 5 and, after decomposition, is directed to a further end use 10. The biogas produced (methane component about 85%) is drawn off and used for producing energy in a consumer 9.

Waste water with a CSB-content of about 300 mg/l exits from the first cleaning stage 5, serves as irrigation in the second cleaning stage, a plant clarifying unit 6, and is transformed to natural organic fertilizer, in a process fed by solar energy, from biomass through photosynthesis.

In process variant A, the plant clarifying unit 6 is formed as an immersion plant that is preferably in the form of a trench for avoiding short circuit currents. As the plant addition, water hyacinth (*eichornia crassipes*) is suitable. This is a highly toxin-resistant plant with a pronounced propagation rate. A 30% addition serves, under suitable climatic conditions, within one month to cover the whole surface and has high take-up rates of nitrogen and toxins.

In process variant B, the plant clarifying unit 6 consists of a land site. It makes no difference which direction, horizontal or vertical, the water flows through the stage in the cleaning step.

Advantageously, a surface treatment of the stage with a horizontal or vertical through-flow is chosen in this variant.

It is, however, also possible to work with a horizontal or vertical through-flow along the stage.

For the process variants, the St Augustine Gras (*stenotaphrum secundatum*) presents itself. It is characterized by very strong plant propagation, salt resistance, and good tolerance to standing water, even over a long time period. In a land treatment this works advantageously for the filter effect of the stage.

The previously mentioned plant types, however, are not in any way exclusive. It is possible to use other plant types as additions in the second cleaning stage.

After flowing through the second cleaning stage, the waste water is cleaned sufficiently such that it meets the requirements for normal use and can be passed directly into receiving streams 7 or can be used for other purposes.

With the process according to the invention it is possible, by corresponding dimensioning of the cleaning stages or by adjusting the through-flow time of the waste water through the first cleaning stage, to achieve, in the exit water from the second cleaning stage, exit values which correspond to or exceed values for conventional clarifying plants.

What is claimed is:

1. A process for cleaning waste water comprising:
   anaerobically treating the waste water in a first cleaning stage with the production of biogas;
   treating the waste water in a plant clarifying unit as a second cleaning stage; and
   introducing biomass gathered from the second cleaning stage into the first cleaning stage in the waste water.

2. The waste water cleaning process according to claim 1, wherein other material in addition to that produced in the second stage plant clarifying unit is introduced into the waste water before the first cleaning stage.

3. The waste water cleaning process according to claim 2, wherein an organic biomass load in the waste water exiting from the first stage is maintained constant.

4. The waste water cleaning process according to claim 2, wherein an organic biomass load in the waste water exiting from the first cleaning stage is controlled by varying the quantity of the other material added to the waste water that flows into the first cleaning stage.

5. The waste water cleaning process according to claim 2, wherein an organic load in the waste water exiting from the first cleaning stage is controlled by the dwell time of the waste water in the first cleaning stage.

6. The waste water cleaning process according to claim 2, wherein an organic biomass load in the waste water exiting from the first cleaning stage is controlled by varying the quantity of biomass and other material added to the waste water that flows into the first cleaning stage.

7. The waste water cleaning process according to claim 1, wherein an organic biomass load in the waste water exiting from the first stage is maintained constant.

8. The waste water cleaning process according to claim 7, wherein the organic biomass load in the waste water exiting from the first cleaning stage is controlled by varying the quantity of the biomass gathered from the second cleaning stage and/or additional organic materials and waste in the waste water that flows into the first cleaning stage.

9. The waste water cleaning process according to claim 7, wherein the organic load in the waste water exiting from the first cleaning stage is controlled by the dwell time of the waste water in the first cleaning stage.

10. The waste water cleaning process according to claim 1, wherein an organic biomass load in the waste water exiting from the first cleaning stage is controlled by varying the quantity of the biomass added to the waste water that flows into the first cleaning stage.

11. The waste water cleaning process according to claim 1, wherein an organic load in the waste water exiting from the first cleaning stage is controlled by the dwell time of the waste water in the first cleaning stage.

12. The waste water cleaning process according to claim 1, wherein organic material in addition to that produced in the second stage plant clarifying unit is added to the waste water that flows into the first cleaning stage.

13. The waste water cleaning process according to claim 1, wherein the biogas is a methane-containing biogas.

14. The waste water cleaning process according to claim 13, further comprising recovering methane from the methane-containing biogas.

15. The waste water cleaning process according to claim 1, wherein the second cleaning stage is an aquatic plant clarifying unit.

16. The waste water cleaning process according to claim 1, wherein the second cleaning stage is a land treatment unit.

* * * * *